(12) United States Patent
Ye

(10) Patent No.: US 11,579,158 B2
(45) Date of Patent: Feb. 14, 2023

(54) AUTOMATIC HUMAN URINE DETECTION SYSTEM

(71) Applicant: Zhejiang Deyeetec Medical Technology Co., Ltd., Zhejiang (CN)

(72) Inventor: Zhi Qian Ye, Zhejiang (CN)

(73) Assignee: ZHEJIANG DEYEETEC MEDICAL TECHNOLOGY CO., LTD., Zhejiang (CN)

( * ) Notice: Subject to any disclaimer, the term of this patent is extended or adjusted under 35 U.S.C. 154(b) by 284 days.

(21) Appl. No.: 16/924,238

(22) Filed: Jul. 9, 2020

(65) Prior Publication Data

US 2021/0018525 A1 Jan. 21, 2021

(30) Foreign Application Priority Data

Jul. 15, 2019 (CN) .......................... 201910635198.3

(51) Int. Cl.
| | |
|---|---|
| *G01N 35/02* | (2006.01) |
| *A61B 10/00* | (2006.01) |
| *B01L 3/00* | (2006.01) |
| *B01L 9/00* | (2006.01) |
| *G01N 21/78* | (2006.01) |

(52) U.S. Cl.
CPC ........... *G01N 35/02* (2013.01); *A61B 10/007* (2013.01); *B01L 3/502* (2013.01); *B01L 3/52* (2013.01); *B01L 3/56* (2013.01); *B01L 3/567* (2013.01); *B01L 9/00* (2013.01); *G01N 21/78* (2013.01); *B01L 2200/0605* (2013.01); *B01L 2200/0621* (2013.01); *B01L 2200/087* (2013.01); *B01L 2200/10* (2013.01); *B01L 2200/16* (2013.01); *B01L 2300/023* (2013.01); *B01L 2300/024* (2013.01); *B01L 2300/0609* (2013.01);

(Continued)

(58) Field of Classification Search
CPC combination set(s) only.
See application file for complete search history.

(56) References Cited

U.S. PATENT DOCUMENTS

| | | | | |
|---|---|---|---|---|
| 2009/0324448 A1* | 12/2009 | Yano | ..................... | G01N 1/4077 422/400 |
| 2020/0309646 A1* | 10/2020 | Qin | ......................... | E03D 11/00 |

FOREIGN PATENT DOCUMENTS

| | | | | |
|---|---|---|---|---|
| WO | WO-2009035599 A1 | * | 3/2009 | ........... A61B 10/007 |
| WO | WO-2015109765 A1 | * | 7/2015 | ........... A61B 10/007 |

* cited by examiner

*Primary Examiner* — Jennifer Wecker
*Assistant Examiner* — Alea N. Martin
(74) *Attorney, Agent, or Firm* — Mark M. Friedman

(57) ABSTRACT

An automatic human urine detection system comprises a control module, a urine collection module, a detection module, an output module and a cleaning module. The control module controls operation of the system and comprises an instruction input unit. The urine collecting module is used for collecting urine to be detected; the detection module comprises a detection probe holder which is used for detecting the urine to be collected and obtains a corresponding detection report according to a detection result; the output module is used for outputting the detection report; and the cleaning module is used for cleaning system components through which the urine flows or is stored in the system. The automatic human urine detection system integrates automatic collection and subsequent automatic detection of human urine, the whole urinalysis process is effectively simplified, the operation process is humanized, and the user experience is good.

9 Claims, 4 Drawing Sheets

(52) U.S. Cl.
CPC ............... *B01L 2300/0663* (2013.01); *B01L 2400/0478* (2013.01); *B01L 2400/0622* (2013.01)

AUTOMATIC HUMAN URINE DETECTION SYSTEM

BACKGROUND OF THE INVENTION

1. Field of the Invention

The present invention relates to medical instruments field, and more particularly to an automatic human urine detection system, which can realize full-automatic collection of human urine and subsequent urine detection, and further outputs a detection result.

2. Description of the Prior Art

With the high-speed development of economy and the increasing improvement of the living standard of people, the attention of people to the health is continuously improved; correspondingly, the physical examination gradually becomes the regular arrangement of people, and the physical examination generally comprises urinalysis.

Common urinalysis, namely so-called 'urine biochemical detection' in the industry, can only be generally completed by professionals in hospitals by adopting professional detection equipment according to urine to be detected provided by personnel to be detected. Therefore, the provided urine to be detected is manually collected by the person to be detected, and the operation experience is not humanized.

Furthermore, the whole urine detection process is artificially divided into two stages, one stage is an artificial urine collection stage, and the other stage is a professional detection stage of the urine to be detected, so that the whole urine detection process is relatively tedious to operate.

Besides, the spatial positions of the two stages involved in the whole detection process are different, and generally, the two stages are located in a toilet and a detection room respectively. In this way, after the person to be detected completes collection of the urine to be detected, the person to be detected needs to send it to a detection room of a professional medical worker for subsequent professional detection. The transfer process has the advantages that on one hand, the condition that the urine to be detected is possibly accidentally damaged occurs, and on the other hand, the complexity of the common urine detection operation in the industry is further aggravated, and the problem of dehumanization in operation is further solved.

Therefore, it is necessary to develop a novel human urine detection system to overcome the defects in the prior art.

BRIEF SUMMARY OF THE INVENTION

Technical Problem

One object of the present invention is to provide an automatic human urine detection system, which can integrate automatic collection and subsequent automatic detection of human urine, effectively simplifies the whole urinalysis process, and has the advantages of humanized operation process and good user experience.

Technical Solutions

To solve the above technical problems, a technical solution of the present invention is as follows.

An automatic human urine detection system comprises a control module, a urine collection module, a detection module, an output module and a cleaning module. The control module controls operation of the system and comprises an instruction input unit. The urine collecting module is used for collecting urine to be detected; the detection module comprises a detection probe holder which is used for detecting the urine to be collected and obtains a corresponding detection report according to a detection result; the output module is used for outputting the detection report; and the cleaning module is used for cleaning system components through which the urine flows or is stored in the system. When an instruction input unit of the control module receives an external instruction, the instruction input unit can inform the urine collection module to start and collect urine, and the detection probe holder of the detection module detects the collected urine and outputs a detection result to the output module to be output. The cleaning module cleans the system components according to the instruction of the control module for reuse.

Further, in different embodiment, the urine collection module comprises a toilet, a urine collection assembly and a urine collection cup; a toilet bowl cavity is defined in the toilet, a urine collecting ditch is defined in the inner wall of the toilet bowl cavity, and a urine collecting opening is defined in the urine collecting ditch. The urine collecting assembly comprises a urine collector, a pipeline and a urine collecting nozzle are disposed in the urine collector, and the pipeline is communicated with the urine collecting nozzle and the urine collecting cup; an upper cover is further disposed on the urine collecting nozzle, and the upper cover is connected with an electromagnetic valve through a linkage assembly; after the electromagnetic valve of the urine collecting module is powered on, the electromagnetic valve can drive the linkage assembly to open the upper cover of the urine collecting nozzle so that the urine to be detected enters into the urine collecting nozzle through the urine collecting opening of the urine collecting ditch and then enters into the urine collecting cup through the pipeline in the urine collector. The toilet can be a pedestal pan or a vertical toilet bowl, and the toilet can be determined according to needs and is not limited.

Further, in different embodiment, the linkage assembly comprises an electromagnetic valve pull rod, a lever connecting piece and a urine collector lever, and a urine collecting piston is disposed in the urine collector; the electromagnetic valve is powered on to generate magnetic force to drive the electromagnetic valve pull rod to be pulled in the direction of the electromagnetic valve, the electromagnetic valve pull rod enables the urine collector lever to rotate through the lever connecting piece so as to drive the urine collecting piston to ascend to open the upper cover of the urine collecting nozzle.

Further, in different embodiment, a liquid level sensor is disposed on one side of the urine collecting cup; when urine to be detected in the urine collecting cup is collected to a preset liquid level, the liquid level sensor can sense the urine and inform the electromagnetic valve to power off. At the moment, under the action of losing electromagnetic force, the electromagnetic valve pull rod is reversely pushed to return to the original position, the electromagnetic valve pull rod is linked with the lever connecting piece to push the urine collector lever to rotate to the original position so that the urine collecting piston descends, and then the upper cover of the urine collecting nozzle retracts and closes the urine collecting nozzle.

Further, in different embodiment, the information sent by the liquid level sensor can also be sent to the control module, and then the control module controls the urine collecting module to be closed, so that the electromagnetic valve is powered off.

Further, in different embodiment, the urine collecting piston further comprises a piston guiding out opening which is communicated with the pipeline in the urine collector, and the collected urine to be detected passes through the piston guiding out opening and then passes through a urine collecting pipe to enter into the urine collecting cup.

Further, in different embodiment, the length of the urine collecting ditch is ½ to ⅕ of the perimeter of the inner wall of the toilet bowl cavity.

Further, in different embodiment, the detection probe holder comprises a sensor assembly and a data processing mainboard, and the sensor assembly comprises a sensor moving transfer plate, a sensor transmitting plate and a sensor receiving plate. The sensor moving transfer plate is used for receiving a detection instruction transmitted from the outside and transmitting the detection instruction to the sensor transmitting plate, the sensor transmitting plate transmits light waves to the urine to be detected. The light waves penetrating through the urine to be detected is received by the sensor receiving plate and a receiving result is sent to the data processing mainboard through the sensor moving transfer plate; the data processing mainboard obtains a detection result of the urine to be detected through data processing.

Further, in different embodiment, the data processing mainboard may also be included into the control modules, but is not limited above.

Furthermore, in different embodiment, the detection probe holder comprises a main body, the main body comprises a first connecting plate, a second connecting plate and a third connecting plate, the second connecting plate and the third connecting plate are symmetrically disposed at both ends of the first connecting plate. A through hole is defined in the first connecting plate. A groove is defined in the outer side surface of the first connecting plate. A pair of probe holder glasses is disposed oppositely on the inner side surface of the second connecting plate and the inner side surface of the third connecting plate; the sensor transmitting plate is disposed on the outer side surface of the second connecting plate, the sensor receiving plate is disposed on the outer side surface of the third connecting plate, the sensor moving transfer plate is disposed on the outer side surface of the first connecting plate, and a probe moving transfer plate guard plate is disposed on the sensor moving transfer plate.

Further, in different embodiment, the detection probe holder further comprises positioning magnetic steel, and the positioning magnetic steel is disposed in the groove; the through hole is connected with a driving screw, and the driving screw is connected with a driving motor. Further, in different embodiment, the detection module further comprises a detection cup used for storing urine to be detected and a detection reagent which are conveyed into the detection cup; the sensor transmitting plate and the sensor receiving plate respectively communicate probe holder glasses, and the sensor transmitting plate, the sensor receiving plate and the probe holder glasses are positioned at the same height as the detection cup; the purpose of detecting the liquid in the detection cup is achieved by utilizing the light intensity transmittance of the color after the reaction of the urine to be detected and the added detection reagent.

Further, in different embodiment, the detection module further comprises a detection reagent delivery metering pump which sucks up the detection reagent stored in a detection reagent storage unit and delivers the detection reagent into the detection cup through reagent distribution pipelines in a probe slider located above the detection cup.

Further, in different embodiment, the urine collection module further comprises a urine distribution metering pump, and the urine collection cup is connected with the urine distribution metering pump and conveys urine to be detected in the urine collection cup into the detection cup through distribution pipelines of the urine distribution metering pump. Further, the number of the detection cups can be multiple, and then the urine distribution metering pump distributes urine of the detection cups through distribution pipelines of the urine distribution metering pump so that multiple different urine detection items can be implemented.

Further, in different embodiment, the cleaning module comprises a first flushing pump which is connected with a first cleaning pipeline, a cleaning nozzle of the first cleaning pipeline is corresponding to the detection cup and the urine collection cup.

Further, in different embodiment, the detection cup and the urine collection cup are disposed on a detection cup support, the cleaning module further comprises a cleaning motor which is connected with the detection cup support through a rotating shaft, the first cleaning pipeline is located below the detection cup support. The number of the cleaning nozzles is two and the cleaning nozzles are corresponding to the detection cup and the urine collection cup respectively. The detection cup support is turned over through rotation of the cleaning motor to pour out waste liquid in the detection cup and the urine collection cup, cleaning liquid is sprayed out through the cleaning nozzle to flush the detection cup and the urine collection cup.

Further, in different embodiment, the cleaning module further comprises a second flushing pump which is connected with a second cleaning pipeline, the second cleaning pipeline is connected with a flushing water inlet of the urine collector, and the flushing water inlet is communicated with a pipeline in the urine collector.

Further, in different embodiment, the cleaning module further comprises a sewage pump which is used for discharging sewage which is stored in the system and used for cleaning all the system components. And for the urine distribution metering pump, the urine distribution metering pump can automatically suck cleaning water to flush the interior of the urine distribution metering pump and a distribution pipeline connected with the urine distribution metering pump according to an instruction.

Further, in different embodiment, the output module comprises a display screen and/or a printer.

Further, in different embodiment, the control module and the output module can be combined together to be implemented by a smart terminal in combination with terminal application software used on the smart terminal. For example, the smart terminal comprises a smart mobile phone, the instruction input unit is terminal APP operation software, the display function of the output module is achieved by a display screen of the smart mobile phone, and the printing function of the output module is achieved by a printer connected with the output module. In other embodiment, the smart terminal can also be a computer terminal or a smart tablet terminal according to needs and is not limited.

Further, in different embodiment, the control module is further connected with a storage module, and a database is contained in the storage module and used for storing the detection report. Furthermore, the storage module can be a cloud storage module, so that the safety of data storage is ensured.

Further, in different embodiment, the detection module further comprises an automatic test paper discharging device, a stepping motor drives a transmission rack to enable a test paper box sealing door to move upwards and open a test paper conveying outlet, and the stepping motor rotates to drive a test paper roll rolling shaft power gear to enable a test paper roll rolling shaft to rotate so as to output test paper outwards. After the detection test paper is output for a preset distance, the stepping motor is turned off, the output of the detection test paper is stopped, and then the stepping motor drives the transmission rack to downwards seal the test paper box sealing door, so that the detection test paper stored inside is in a sealed state. The urine distribution metering pump of the urine collection module is connected with the urine collection cup, urine to be detected in the urine collection cup is conveyed to the position above the output detection test paper through a water outlet pipe of the urine distribution metering pump and drips onto the detection test paper, and the detection probe holder detects the area that the urine to be detected is dripped onto.

Beneficial Effect

The beneficial effect of the present invention is that: an automatic human urine detection system integrates automatic collection and subsequent automatic detection of human urine, the whole urinalysis process is effectively simplified, the operation process is humanized, and the user experience is good.

Further, the automatic human urine detection system can be used in combination with a mobile terminal, such as a mobile phone, so that the automatic human urine detection system is convenient to operate and wide in application range.

DETAILED DESCRIPTION OF THE PREFERRED EMBODIMENTS

The following text will clearly and completely describe preferred embodiment of the present invention with reference to the accompanying drawings, in order to fully introduce the technical contents of the present invention to technicians in the field, and to demonstrate with examples that the present invention can be implemented, so as to make the technical contents of the present invention clearer and make it easier for technicians in the field to understand how to implement the present invention. However, the present invention can be embodied by many different forms of embodiments. The protection scope of the present invention is not limited to the embodiments mentioned herein, and the description of the embodiments below is not intended to limit the scope of the present invention.

Figure 1:
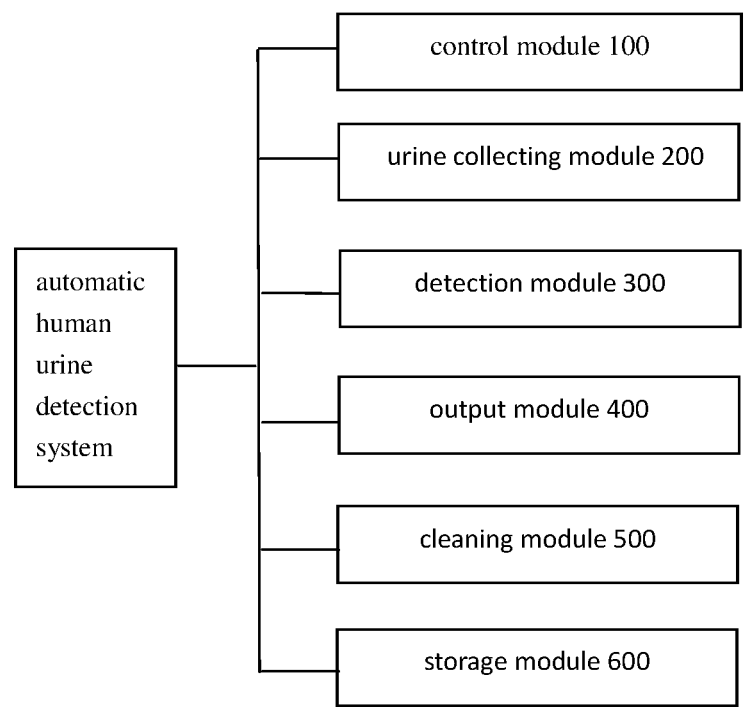
FIG. 1 is a logic structure schematic diagram of an automated human urine detection system provided by one embodiment of the present invention.

Please refer to FIG. 1, one embodiment of the invention provides an automatic human urine detection system, which comprises a control module 100, a urine collection module 200, a detection module 300, an output module 400, a cleaning module 500 and a storage module 600.

The control module 100 controls automatic operation of automation system according to the present invention and comprises an instruction input unit. The urine collecting module 200 is used for collecting urine to be detected; the detection module 300 comprises a detection probe holder which is used for detecting the urine to be collected and obtains a corresponding detection report according to a detection result; the output module 400 is used for outputting the detection report; and the cleaning module 500 is used for cleaning system components through which the urine flows or is stored in the system. The storage module 600 is used for storing a detection report, and a database is contained in the storage module 600 and used for storing the detection report.

When an instruction input unit of the control module 100 receives an external instruction, the instruction input unit can inform the urine collection module 200 to start and collect urine, and instruct a detection probe holder of the detection module 300 to detect the collected urine. After the detection module 300 completes detection, a detection result is output to the output module 400 for outputting and is also transmitted to the storage module 600 for data storage at the same time. The cleaning module 500 cleans used system components according to an instruction of the control module 100 for reuse. The detection report output of the detection module 300 can be automatically carried out according to the internal setting of the module, can also be carried out according to the instruction of the control module 100, it can be determined according to the need, is not limited, but is within the protection scope of the present invention.

Details of the modules will be described below in connection with the FIGS.

The detailed embodiments of the control module can be in various types, such as a single-chip microcomputer type, a computer terminal type, a smart mobile terminal type and the like.

In one embodiment, the control module 100, the output module 400 and the storage module 600 are combined together to be implemented by a smart terminal in combination with terminal application software used on the smart terminal. For example, the smart terminal comprises a smart mobile phone, the instruction input unit is terminal APP operation software, the display function of the output module is achieved by a display screen of the smart mobile phone, and the printing function of the output module is achieved by a printer connected with the output module, the storage module 600 is implemented by a mobile phone memory card. In other embodiment, the smart terminal can also be a computer terminal or a smart tablet terminal according to needs and is not limited.

The urine collection module comprises a toilet, a urine collection assembly and a urine collection cup. Please refer to FIG. 2, in this embodiment, the toilet can be a pedestal pan 101, a toilet bowl cavity 102 is defined in the pedestal pan 101, a urine collecting ditch 103 is defined in the inner wall of the toilet bowl cavity 102, and a urine collecting opening 104 is defined in the urine collecting ditch.

Figure 3:
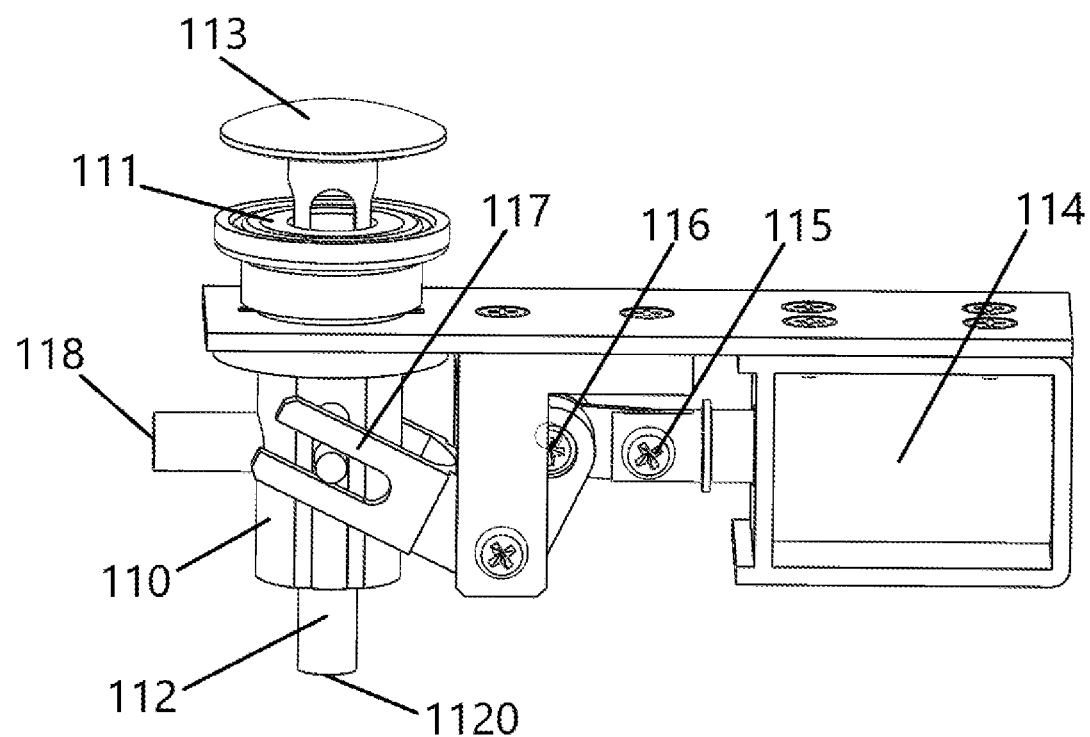
FIG. 3 is a structural schematic view of a urine collection assembly in the urine collection module of the automatic human urine detection system shown in FIG. 1.
Figure 4:
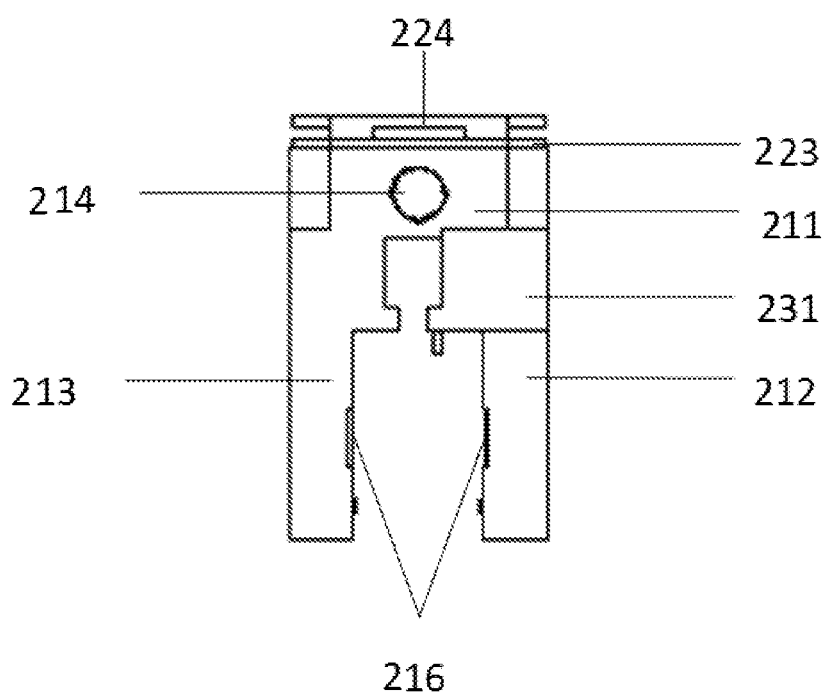
FIG. 4 is a structural schematic view of a detection probe holder in detection module of automatic human urine detection system shown in FIG. 1.
Figure 5:
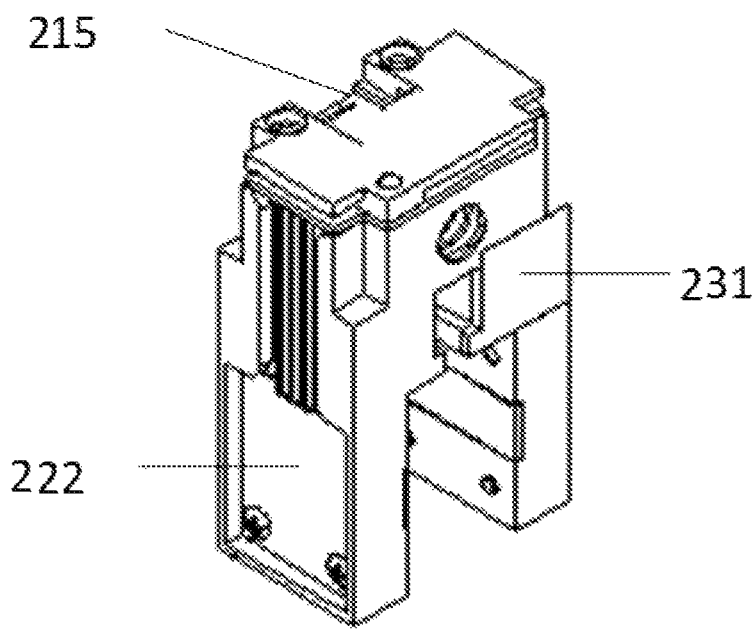
FIG. 5 is a structure schematic view of the detection probe holder shown in FIG. 4 from another angle.
Figure 6:
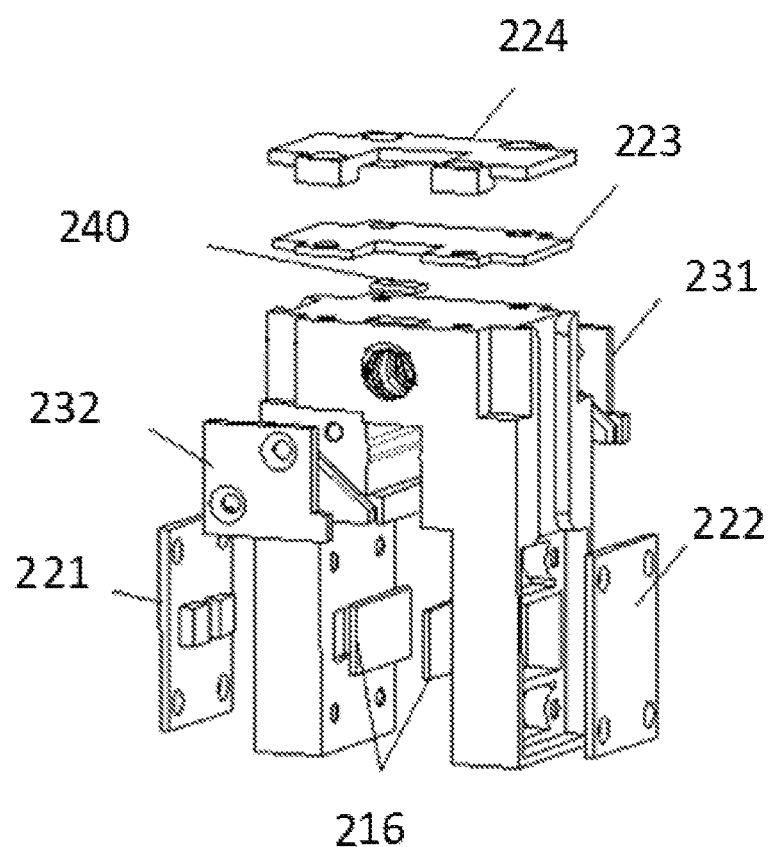
FIG. 6 is an exploded schematic view of the detection probe holder shown in FIG. 4.
Figure 7:
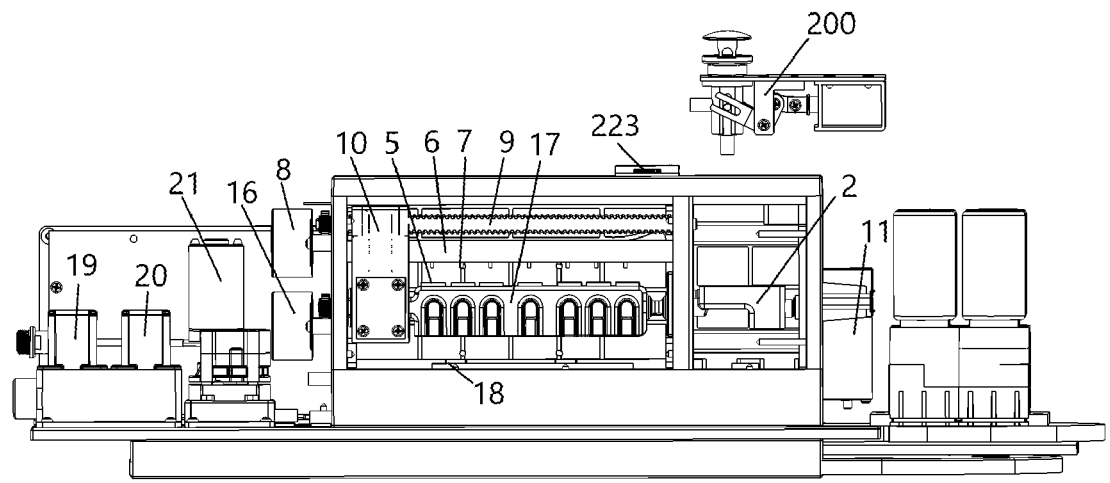
FIG. 7 is a structural schematic view of the automatic human urine detection system shown in FIG. 1.

Referring to FIG. 3 and shown in connection with FIG. 7, the urine collection assembly comprises a urine collector 110 having a urine collection nozzle 111, a urine collection piston 112, and an internal pipelines. The internal pipelines communicates with the urine collection nozzle 111 and the urine collection piston 112. An upper cover 113 is further disposed on the urine collecting nozzle 111, and the upper cover 113 is connected with an electromagnetic valve 114 through a linkage assembly.

The linkage assembly comprises an electromagnetic valve pull rod 115, a lever connecting piece 116 and a urine collector lever 117. The electromagnetic valve 114 is powered on to generate magnetic force to drive the electromagnetic valve pull rod 115 to be pulled in the direction of the electromagnetic valve 114, the electromagnetic valve pull rod 115 enables the urine collector lever 117 to rotate through the lever connecting piece 116 so as to drive the urine collecting piston 112 to ascend to open the upper cover 113 of urine collecting nozzle, and then urine to be detected passing through the urine collecting opening can enter into the urine collecting nozzle 111.

The urine collecting piston 112 further comprises a piston guiding out opening 1120 which is communicated with pipelines in the urine collector 110, and the collected urine to be detected passes through the piston guiding out opening 1120 and then passes through a urine collecting pipe to enter into the urine collecting cup 2 (shown in FIG. 7). The urine collector 110 is further provided with a cleaning opening 118 so that external clean water can be introduced subsequently from it when cleaning the components that the urine flows through.

Liquid level sensor are disposed on both sides of the urine collecting cup 2 (shown in FIG. 7), when urine to be detected in the urine collecting cup is collected to a preset liquid level, the liquid level sensor can sense the urine and inform the electromagnetic valve 114 to power off. At the moment, under the action of losing electromagnetic force, the electromagnetic valve pull rod 115 is reversely pushed to return to the original position, the electromagnetic valve pull rod 115 is linked with the lever connecting piece 116 to push the urine collector lever 117 to rotate to the original position so that the urine collecting piston 112 descends, and then the upper cover of the urine collecting nozzle retracts and closes the urine collecting nozzle.

In different embodiments, the information sent by the liquid level sensor can also be sent to the control module, and then the control module controls the urine collecting module to be closed, so that the electromagnetic valve is powered off.

Refer to FIG. 7, the detection module comprises a detection probe holder 10, a detection cup 5 and a detection reagent delivery metering pump 4. And the detection cup 5 is used for storing urine to be detected and a detection reagent which are conveyed into the detection cup 5. The detection reagent conveying metering pump is used for sucking the detection reagent stored in a detection reagent storage unit, and the detection reagent is conveyed into the detection cup 5 through a reagent distribution pipeline 7 in a probe sliding block 6 located above the detection cup 5. The detection cup 5 and the urine collection cup 2 can be disposed on a detection cup support 17.

Further, in different embodiments, the urine collection module further comprises a urine distribution metering pump 11 (shown in FIG. 7), and the urine collection cup 2 is connected with the urine distribution metering pump and conveys urine to be detected in the urine collection cup 2 into the detection cup through distribution pipelines of the urine distribution metering pump. Further, the number of the detection cups can be multiple, and then the urine distribution metering pump distributes urine of the detection cups through distribution pipelines of the urine distribution metering pump so that multiple different urine detection items can be implemented.

The detection probe holder comprises a main body, a sensor assembly and a data processing mainboard. Refer to FIG. 4-FIG. 8, the main body further comprises a first connecting plate 211, a second connecting plate 212 and a third connecting plate 213, the second connecting plate 212 and the third connecting plate 213 are symmetrically disposed at both ends of the first connecting plate 211. A through hole 214 is defined in the first connecting plate 211. A groove 215 is defined in the outer side surface of the first connecting plate 211. A pair of probe holder glasses 216 is disposed oppositely on the inner side surface of the second connecting plate and the inner surface of the third connecting plate. The probe holder glass 216 is made of a colorless transparent organic material to actually reflect the light intensity effect in the detection process.

Refer to FIG. 7, the through hole 214 is connected with a driving screw 9, the through hole 214 is a threaded hole, the through hole 214 is in threaded sliding connection with the driving screw 9. The driving screw 9 is connected with a driving motor 8, the driving motor 8 drives the driving screw 9 to enable the detection probe holder 10 to slide along the length direction of the driving screw 9. The groove 215 is used for installing a positioning piece 240, the positioning piece 240 is positioning magnetic steel, and the positioning magnetic steel is used for positioning, so that the driving motor 8 and the driving screw 9 drive the detection probe seat 10 to move to a specified position and then to be fixed.

The main body is further provided with a first cover plate 231 and a second cover plate 232, the first cover plate 231 is disposed on the outer side surface of the second connecting plate 12, the second cover plate 232 is disposed on the outer side surface of the third connecting plate 213, the first cover plate 231 and the second cover plate 232 are disposed in parallel and used for fixing a liquid conveying pipeline.

The sensor assembly comprises a sensor transmitting plate 221, a sensor receiving plate 222, a sensor moving transfer plate 223 and a probe moving transfer plate guard plate 224. The sensor transmitting plate 221 is disposed on the outer side surface of the second connecting plate 212, and the sensor transmitting plate 221 is used for emitting light intensity. The sensor receiving plate 222 is disposed on the outer side surface of the third connecting plate 213 and is used for receiving light intensity. The sensor moving transfer plate 223 is disposed on the outer side surface of the first connecting plate 211 and connected with the sensor transmitting plate 221 and the sensor receiving plate 222 by wire harnesses. The probe moving transfer plate protection plate 224 is disposed on the sensor moving transfer plate 223 so as to protect the sensor moving transfer plate 223.

The sensor transmitting plate 221 and the sensor receiving plate 222 respectively communicate the probe holder glasses 216, and the sensor transmitting plate 221, the sensor receiving plate 222 and the probe holder glasses 216 are positioned at the same height as the detection cup. The purpose of detecting the liquid in the detection cup is achieved by utilizing the light intensity transmittance of the color after the reaction of the urine to be detected and the added detection reagent.

The sensor moving transfer plate 223 is used for receiving a detection instruction transmitted from the outside and transmitting the detection instruction to the sensor transmitting plate 221, and the sensor transmitting plate 221 transmits light waves to urine to be detected. The light wave penetrating through the urine to be detected is received by the sensor receiving plate 222 and a receiving result is sent to the data processing mainboard 15 (shown in FIG. 8) through the sensor moving transfer plate 223; and the data processing mainboard 15 obtains a detection result of the urine to be detected through data processing.

The cleaning module comprises a first flushing pump 19 which is connected with a first cleaning pipeline 18 (shown in FIG. 7), and the cleaning nozzle of the first cleaning pipeline corresponds to the detection cup and the urine collection cup. The detection cup and the urine collection cup are disposed on a detection cup support 17 (shown in FIG. 7). The cleaning module further comprises a cleaning motor 16 (shown in FIG. 7) which is connected with the detection cup support 17 through a rotating shaft, the first cleaning pipeline is located below the detection cup support. The number of the cleaning nozzles is two and the cleaning nozzles correspond to the detection cup and the urine collection cup respectively.

Further, the cleaning module further comprises a second flushing pump 20 (shown in FIG. 7) which is connected with a second cleaning pipeline, the second cleaning pipeline is connected with a flushing water inlet 118 of the urine collector, and the flushing water inlet 118 is communicated with a pipeline in the urine collector. The cleaning module further comprises a sewage pump 21 (shown in FIG. 7) which is used for discharging sewage which is stored in the system and used for cleaning all the system components. And for the urine distribution metering pump, the urine distribution metering pump can automatically suck cleaning water to flush the interior of the urine distribution metering pump and a distribution pipeline connected with the urine distribution metering pump according to an instruction.

Figure 8:
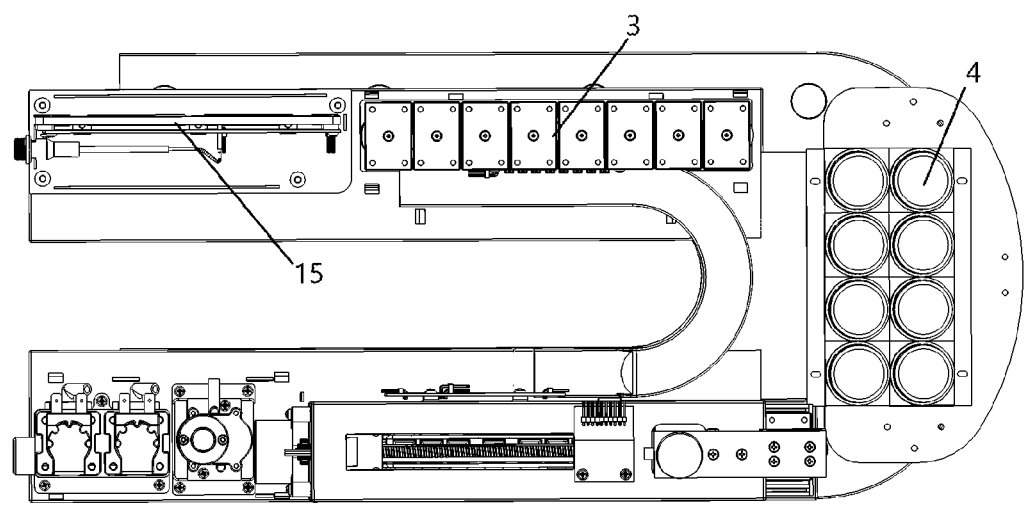
FIG. 8 is a structural schematic of the automatic human urine detection system shown in FIG. 7 from another angle.

Refer to FIG. 7 and FIG. 8, detailed functional descriptions of the automatic human urine detection system of the present invention will be made below.

The automatic human urine detection system is in a working state. When the urine of a human body needs to be detected, APP software or application operation software running on a display device of a smart phone, a smart tablet or an intelligent terminal is started firstly to send a urine detection instruction, and at the moment, after receiving the operation instruction, the control module instructs the urine collection module to be started; and the human urine then enters into the urine collecting ditch of the pedestal pan.

When the urine collecting module is started, the electromagnetic valve 114 is powered on to generate magnetic force to drive the electromagnetic valve pull rod 115 to be pulled in the direction of the electromagnetic valve 114, the pull rod 115 enables the urine collector lever 117 to rotate through the lever connecting piece 116, and then the urine collecting piston 112 is driven to ascend so that the upper cover 113 of the urine collecting nozzle can be opened upwards. At the moment, the position of the urine collecting nozzle 111 in the opening state is lower than the position of the urine collecting opening 104.

Figure 2:
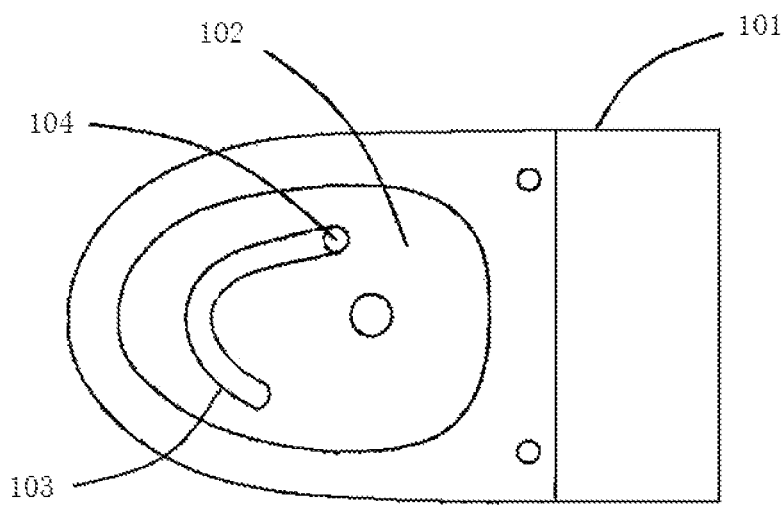
FIG. 2 is a structural schematic view of a pedestal pan in a urine collection module of the automatic human urine detection system shown in FIG. 1.

Refer to FIG. 2 and FIG. 3, as the urine collecting groove 103 is preferably designed to be U-shaped, and the urine collecting opening 104 is positioned at the bottom-most part of the urine collecting groove 103, urine can be automatically gathered to the urine collecting opening 104 through the urine collecting groove 103 and then enters into the urine collecting nozzle 111; and the urine flows into the urine collection cup 2 through the urine collection piston lead-out port 1120 via the urine collector internal pipeline.

When urine is collected to a preset liquid level, the liquid level sensors disposed on both sides of the urine collecting cup 2 can sense the liquid level, then the electromagnetic valve 114 is notified to be powered off. The electromagnetic valve pull rod 115 is reversely pushed to return to the original position after the effect of electromagnetic force is lost, and the electromagnetic valve pull rod 115 pushes the urine collector lever 117 to rotate to the original position through the lever connecting piece 116 so that the urine collection piston 112 descends, the upper cover 113 of the urine collection nozzle is retracted to seal the urine collection nozzle 111, and subsequent urine cannot enter into the urine collection nozzle 111 and can flow to the urinal outlet through the flow guide outlet of the pedestal pan to be discharged.

Subsequently, according to an instruction of the control module, introduced external clear water can flush the urine collecting ditch 103 and the urine collecting opening 104, and meanwhile, introduced internal clear water flowing through the urine collecting module flushing water inlet 118 can automatically flush components which are involved in the urine collector and through which urine flows through, so that the components can be used next time. Thereby, the whole collection process of the human urine to be detected is automatically completed, bacterial pollution is avoided, and pollution among different human urine is also avoided.

The reagent conveying metering pump 3 in the detection module can suck reagent in the reagent storage module 4, and the reagent is distributed into the corresponding detection cup 5 through reagent distribution pipelines 7 in a probe sliding block 6 located above the detection cup 5. The driving motor 8 drives the driving screw 9 to lead the detection probe holder 10 connected with the driving screw 9 to slide to the position above the detection cup 5, the positioning magnetic steel 240 on the detection probe holder 10 is positioned in the moving process, and it is guaranteed that liquid is conveyed and detected at the correct position.

At the moment, the urine in the urine collection cup 2 is conveyed to a urine dripping opening in the detection probe holder 10 through a water outlet pipe of the urine distribution metering pump 11 to be distributed into the detection cup 5, the detection probe holder 10 starts to detect, the sensor moving transfer plate 223 included in the detection probe seat 10 transfers a detection instruction to the sensor transmitting plate 221; the sensor transmitting plate 221 transmits light waves, the light waves penetrating through the liquid are received by the sensor receiving plate 222, the result is sent to the data processing mainboard 15 through the sensor moving holder plate 223, and the detection result obtained from processing of the data processing mainboard 15 is sent to the display terminal to be displayed. Meanwhile, the detection result can be sent to printing equipment to be printed.

After the detection is finished, the components related to the flowing through and storage of the urine to be detected in the system are cleaned. The cleaning motor 16 drives a rotating shaft to lead the detection cup bracket 17, the detection cup 5 disposed on the detection cup bracket 17 and the urine collection cup 2 to turn over by 180 degrees. Due to the first cleaning pipeline 18 is located under the detection cup support 17, the first cleaning pipeline 18 is provided with the cleaning spray holes correspondly facing the detection cup 5 and the urine collection cup 2, one outlet of the first flushing pump 19 is connected with the first cleaning pipeline 18 so as to flush the detection cup 5 and the urine collection cup 2. The urine distribution metering pump 11 automatically sucks clean water to flush the interior of the urine distribution metering pump 11 and the connected urine distribution pipelines. As described in the urine collecting process of the urine collecting module, an outlet of the second flushing pump 20 is connected with the flushing opening 118 of the urine collecting module so as to flush the urine flowing channel in the urine collecting module. The sewage pump 21 is used for emptying the cleaned used sewage to wait for the next detection.

According to the automatic human urine detection system, which integrates automatic collection and subsequent automatic detection of human urine, the whole urinalysis process is effectively simplified, the operation process is humanized, and the user experience is good.

The automatic human urine detection system can be used in combination with a mobile terminal, such as a mobile phone, so that the automatic human urine detection system is convenient to operate and wide in application range.

The above is only the preferred embodiment of the present invention. It should be pointed out that for ordinary technicians in the technical field, without departing from the principles of the present invention, a number of improvements and finishing can also be made, and these improvements and finishing should also be considered as the scope of protection of the present invention.

What is claimed is:

1. An automatic human urine detection system, comprising:
    a control module, controlling operation of the automatic human detection system and comprising an instruction input unit;
    a urine collecting module, being used for collecting urine to be detected;
    a detection module, comprising a detection probe holder for detecting the urine to be collected and obtaining a corresponding detection report according to a detection result;
    an output module, being used for outputting the detection report; and
    a cleaning module, being used for cleaning system components through which the urine flows or is stored in the system;
    wherein, when an instruction input unit of the control module receives an external instruction, the instruction input unit informs the urine collection module to start and collect urine, the detection probe holder of the detection module detects the collected urine and outputs a detection result to the output module to be output, the cleaning module cleans the system components according to instruction of the control module for reuse;
    wherein the urine collection module comprises a toilet, a urine collection assembly and a urine collection cup; the toilet defining a toilet bowl cavity and the toilet bowl cavity comprising a urine collecting ditch defined in an inner wall of the toilet bowl cavity, the urine collecting ditch defining a urine collecting opening; the urine collection assembly comprises a urine collector, a pipeline and a urine collecting nozzle are disposed in the urine collector, and the pipeline is communicated with the urine collecting nozzle and the urine collecting cup; an upper cover is further disposed on the urine collecting nozzle, and the upper cover is connected with an electromagnetic valve through a linkage assembly;
    wherein, after the electromagnetic valve of the urine collecting module is powered on, the electromagnetic valve can drive the linkage assembly to open the upper cover of the urine collecting nozzle so that the urine to be detected enters into the urine collecting nozzle through the urine collecting opening of the urine collecting ditch and then enters into the urine collecting cup through the pipeline in the urine collector.

2. The automatic human urine detection system as claimed in claim 1, wherein the linkage assembly comprises an electromagnetic valve pull rod, a lever connecting piece and a urine collector lever, and a urine collecting piston is disposed in the urine collector; the electromagnetic valve is powered on to generate magnetic force to drive the electromagnetic valve pull rod to be pulled in the direction of the electromagnetic valve, the electromagnetic valve pull rod enables the urine collector lever to rotate through the lever connecting piece so as to drive the urine collecting piston to ascend to open the upper cover of the urine collecting nozzle.

3. The automatic human urine detection system as claimed in claim 1, wherein a liquid level sensor is disposed on one side of the urine collecting cup; when urine to be detected in the urine collecting cup is collected to a preset liquid level, the liquid level sensor can sense the urine and inform the electromagnetic valve to power off.

4. The automatic human urine detection system as claimed in claim 3, wherein the urine collecting piston further comprises a piston guiding out opening which is communicated with the pipeline in the urine collector, and the collected urine to be detected passes through the piston guiding out opening and then passes through a urine collecting pipe to enter into the urine collecting cup.

5. The automatic human urine detection system as claimed in claim 1, wherein the detection probe holder comprises a sensor assembly and a data processing mainboard, the sensor assembly comprises a sensor moving transfer plate, a sensor transmitting plate and a sensor receiving plate; the sensor moving transfer plate is used for receiving a detection instruction transmitted from the outside and transmitting the detection instruction to the sensor transmitting plate, and the sensor transmitting plate transmits light waves to the urine to be detected, the light waves penetrating through the urine to be detected is received by the sensor receiving plate and a receiving result is sent to the data processing mainboard through the sensor moving transfer plate; the data processing mainboard obtains a detection result of the urine to be detected through data processing.

6. The automatic human urine detection system as claimed in claim 5, wherein the detection module further comprises a detection cup used for storing urine to be detected and a detection reagent which are conveyed into the detection cup; the urine collection module further comprises a urine distribution metering pump, and the urine collection cup is connected with the urine distribution metering pump and conveys the urine to be detected in the urine collection cup into the detection cup through distribution pipelines of the urine distribution metering pump; the detection module further comprises a detection reagent delivery metering pump which sucks up the detection reagent stored in a detection reagent storage unit and delivers the detection reagent into the detection cup through reagent distribution pipelines in a probe slider located above the detection cup; the sensor transmitting plate and the sensor receiving plate respectively communicate probe holder glasses, and the sensor transmitting plate, the sensor receiving plate and the probe holder glasses are positioned at the same height as the detection cup; the purpose of detecting the liquid in the detection cup is achieved by utilizing the light intensity transmittance of the color after the reaction of the urine to be detected and the added detection reagent.

7. The automatic human urine detection system as claimed in claim 6, wherein the cleaning module comprises a first flushing pump which is connected with a first cleaning pipeline, a cleaning nozzle of the first cleaning pipeline is corresponding to the detection cup and the urine collection cup; the detection cup and the urine collection cup are disposed on a detection cup support, the cleaning module further comprises a cleaning motor which is connected with the detection cup support through a rotating shaft, the first cleaning pipeline is located below the detection cup support; the number of the cleaning nozzles is two and the cleaning nozzles are corresponding to the detection cup and the urine collection cup respectively; the detection cup support is turned over through rotation of the cleaning motor to pour out waste liquid in the detection cup and the urine collection cup, cleaning liquid is sprayed out through the cleaning nozzle to flush the detection cup and the urine collection cup.

8. The automatic human urine detection system as claimed in claim 1, wherein the output module comprises a display screen and/or a printer; the control module is further connected with a storage module, and a database is contained in the storage module and used for storing the detection report, The automatic human urine detection system as claimed in claim 1, wherein the control module and the output module can be combined together to be implemented by a smart terminal in combination with terminal application software used on the smart terminal.

9. The automatic human urine detection system as claimed in claim 1, wherein the control module and the output module can be combined together to be implemented by a terminal in combination with terminal application software used on the terminal.

* * * * *